United States Patent [19]
Leonard et al.

[11] Patent Number: 4,935,367
[45] Date of Patent: Jun. 19, 1990

[54] NOVEL RESTRICTION ENDONUCLEASE

[75] Inventors: Warren J. Leonard, Bethesda; Julie B. Wolf, Columbia, both of Md.; Nancy F. Halden, Reston, Va.

[73] Assignee: The United States of America as represented by the Department of Health and Human Services, Washington, D.C.

[21] Appl. No.: 260,829

[22] Filed: Oct. 21, 1988

Related U.S. Application Data

[63] Continuation-in-part of Ser. No. 169,487, Mar. 17, 1988.

[51] Int. Cl.⁵ .................... C12N 9/22; C12P 19/34; C12R 1/35
[52] U.S. Cl. .................... 435/199; 435/91; 435/870
[58] Field of Search .................. 435/199, 91, 870, 19, 435/6, 34, 35, 810

[56] References Cited

PUBLICATIONS

Tung, C.-S., et al. (1986) J. Biol. Chem. 261(8), 3700–3709.
Tate (1987) Nucl. Acids Res 15(16), 6739.

Primary Examiner—Thomas G. Wiseman
Assistant Examiner—Charles L. Patterson, Jr.
Attorney, Agent, or Firm—Mishrilal Jain

[57] ABSTRACT

A new restriction enzyme, Mfe I, has been discovered. Mfe I recognizes the sequence CAATTG and cuts at the recognition sequence C'AATTG and generates compatible cohesive ends with EcoRI cleaved fragments. Various utilities of the enzyme have been described.

2 Claims, 5 Drawing Sheets

```
5'-ACCCCAGCCCACACCTCCAGCAATTGAACTTGAAAAAAAAACCTG-3"
3'-TGGGGTCGGGTGTGGAGGTCGTTAACTTGAACTTTTTTTTTGGAC-5'
```

OLIGO 1

```
5'-GAATTCGAGCTCGCCCGGGATCCCAGCAATTGAACTTCTAGAGTCGACCTGCAGCCCAAGCTT-3'
3'-CTTAAGCTCGAGCGGGCCCTAGGGTCGTTAACTTGAAGATCTCAGCTGGACGTCGGGTTCGAAA-5'
                                ****
```

OLIGO 2

```
5'-GAATTCGAGCTCGCCCGGGATCGGCCCCTAGAGTCGACCTGCAGCCCAAGCTT-3'
3'-CTTAAGCTCGAGCGGGCCCTAGCCGGGGATCTCAGCTGGACGTCGGGTTCGAA-5'
       ****
```

NOVEL RESTRICTION ENDONUCLEASE

This is a continuation in part of the pending application Ser No. 07/169,487 filed Mar. 17, 1988.

The present invention is related generally to the family of restriction enzymes. More particularly, the present invention is related to the identification, characterization and preparation of a site-specific restriction endonuclease, designated herein as Mfe I, which specifically recognizes the nucleotide sequence CAATTG and cleaves between the C and the first A within the sequence CAATTG. No such enzyme has heretofore been known or described.

SUMMARY OF THE INVENTION

It is, therefore, an object of the present invention to provide a novel restriction enzyme.

It is a further object of the present invention to provide a diagnostic test for mycoplasma.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 shows recognition and cutting by the nuclease specifically at C'AATTG. FIG. 2A: Shown are the sequences of the region of the IL2Rα promoter containing the cleavage site (−195/−150) and synthetic oligonucleotides sharing (oligo 1) or not sharing (oligo 2) extra bases beyond the palindrome CAATTG. The radiolabeled bases after filling in 5' overhangs are indicated by asterisks. Both oligonucleotides were cleaved within the palindrome.

DETAILED DESCRIPTION OF THE INVENTION

The above and various other objects and advantages of the present invention are achieved by Mfe I, a biologically isolated restriction endonuclease which recognizes the palindrome CAATTG and cleaves it between the C and the first A of the palindrome.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Although Mfe I can be produced by chemical synthetic and recombinant DNA technologies and the like, a preferred source of the enzyme is mycoplasma, particularly *Mycoplasma fermentans*.

Purification of Mfe I

Mfe I is purified from *M. fermentans* as follows. The mycoplasma is grown in suitable medium (following instructions contained in the ATCC catalog of Bacteria, Phages, and rDNA vectors and the ATCC Media Handbook) and extracts prepared. Such extracts are concentrated by standard precipitation technique using ammonium sulfate and then passed over a Sephacryl S300 gel filtration column. The active fractions are pooled and then applied to a heparin agarose column in 0.1M KCl. The column is then eluted sequentially with buffer containing 0.2M, 0.3M, 0.4M, 0.5M, and 1.0M KCl. The active fraction is then diluted to 50 mM KCl and purified using FPLC Mono S column (cation exchange column). A linear gradient from 0.05M to 0.3M KCl is applied to elute the protein. The protein is then further enriched by DNA-affinity chromatography using concatamerized double stranded DNA consisting of the sequence:

5'-GATCCCAATTGGATC-3'

3'-GGTTAACCTAGCTAG-5' which contains the recognition site for binding the protein. The protein is eluted using a gradient of 0.1 to 0.5M KCl. In this fashion biologically isolated and purified Mfe I is obtained.

Figure 1:
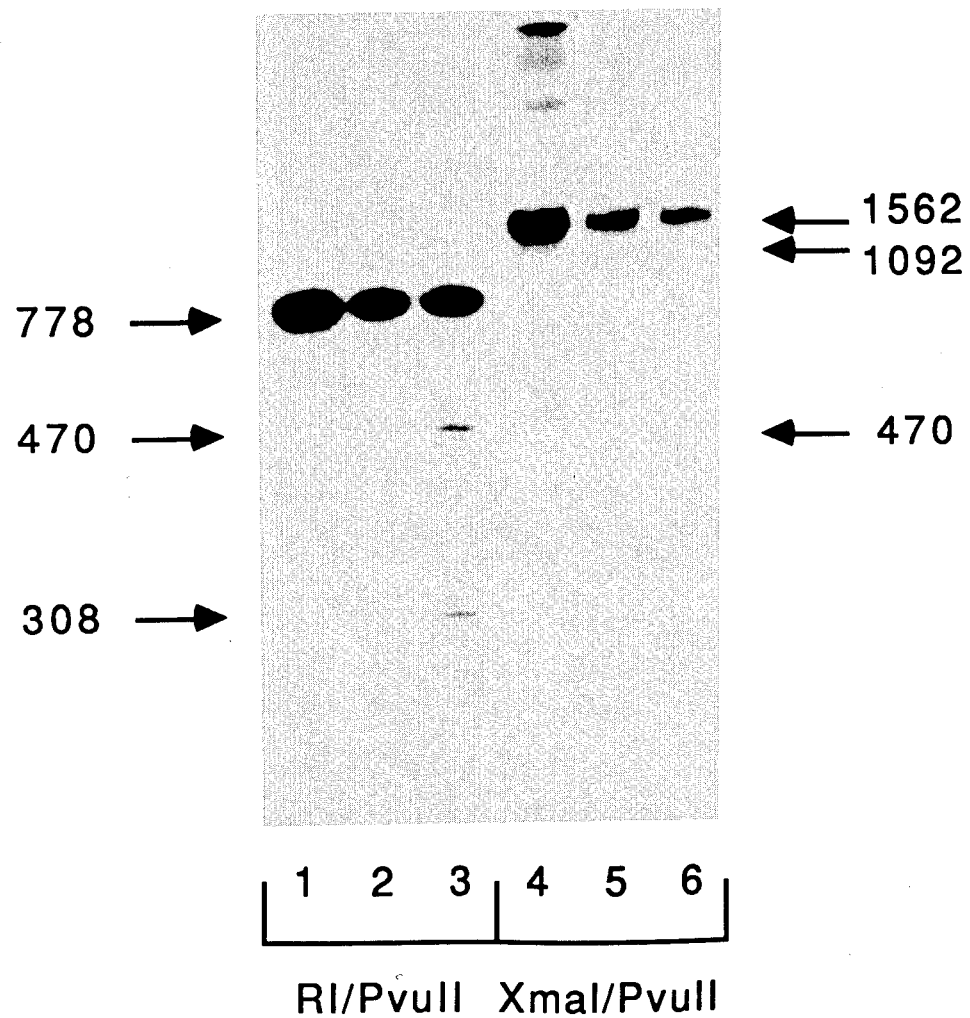
FIG. 1 demonstrates site specific nuclease activity in Jurkat extracts. The EcoRI/PstI (−481/+109) (lanes 1-3) and PstI/PstI (−1242/+109) (lanes 4-6) IL2R promoter fragments (Cross, et al. Cell 49:47-56 1987) were cloned in pUC13; the plasmids digested with EcoRI plus PvuII or XmaI plus PvuII, respectively, to liberate the promoter and the adjacent lac op region. The fragments (778 and 1562 bp respectively) were end-labeled with $^{32}$P, the lac repressor/beta galactosidase fusion protein bound, and the fragments immunoprecipitated with anti-betagalactosidase antibodies. These labeled DNA fragements were then incubated with no extracts (lanes 1,4), HUT-102B2 extracts (lanes 2,5) or Jurkat extracts (lanes 3,6). Samples were then extracted with phenol/chloroform, ethanol precipitated, and analyzed on 8M urea, 6% polyacrylamide gels by autoradiography.

It may be noted here that in order to test and determine various parameters governing the optimal activity of the enzyme, the nuclear extract per se from mycoplasma contaminated cells may be utilized without further purification of the enzyme. As shown in FIG. 1, the extracts prepared from Jurkat cells contained a nuclease activity not present in those from HUT-102B2 cells, an HTLV-I transformed T cell line. Each of the DNA fragments was cleaved once at a specific location suggesting site specific nuclease activity. The band of 470 bases is produced after cleavage of each DNA probe, indicating that it contained the shared 3' terminus.

Next, extracts from several other cell types were prepared to evaluate whether the activity was specific to Jurkat cells. Similar activity was detected in HTLV-I transformed MT-2 T cells (shown in FIG. 3, lane 16, with a different DNA construct) and in Jurkat cells induced with phorbol myristate acetate, but not in CEM T bells or HeLa cells (data not shown). It may be noted here that the endonuclease activity was found to be associated with the presence of *Mycoplasma fermentans*.

Figure 2B:
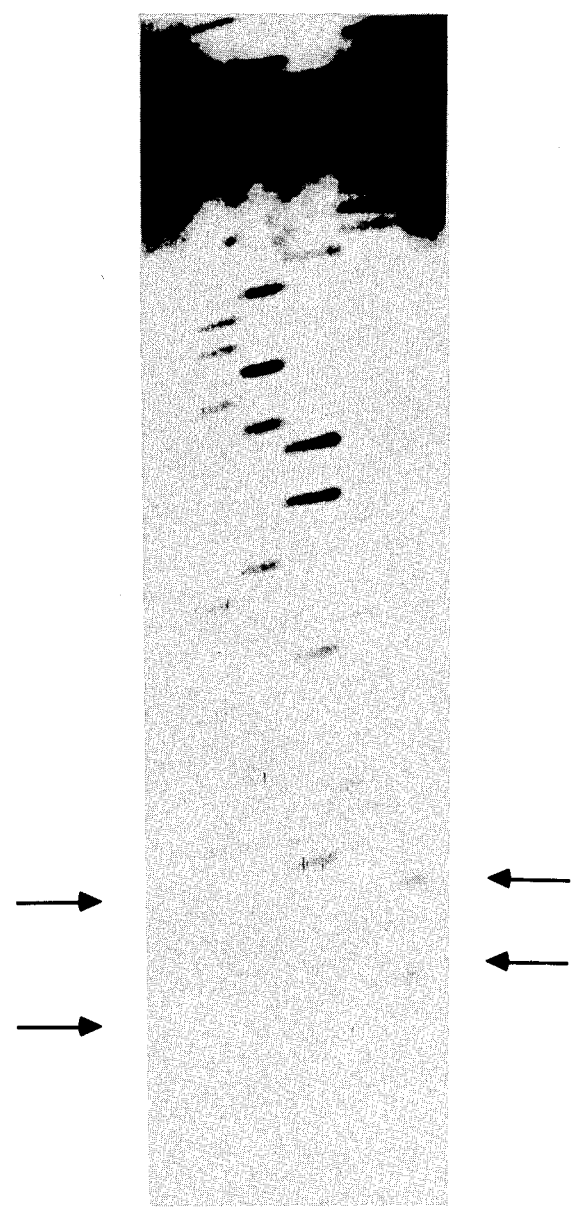
FIG. 2B: Fragments were cloned and labeled as described herein infra. Oligo 1 (lane 1) and oligo (lane 2) were then incubated with Jurkat extracts, followed by extraction with phenol/chloroform, ethanol precipitation and analysis as in FIG. 1 on denaturing gels. The lanes marked G, A, T, and C represent a dideoxy sequencing ladder generated by using M13mp18 and the 17 base universal sequencing primer.

Based on the size of the fragments generated (FIG. 1), the putative cleavage site to the palindrome CAATTG was mapped. To confirm that this six base sequence was sufficient for recognition and cleavage, two synthetic double stranded oligonucleotides were prepared on a DNA synthesizer (Applied Biosystems Model 381A). Each contained BamHI/XbaI compatible cohesive ends and was thus cloned into the pUC13 polylinker. In FIG. 2A, the top sequence indicates the sequence in the IL-2 receptor alpha chain promoter from −195 to −150. The second and third sequences represent the sequence obtained after digesting the pUC13 polylinker containing the synthetic oligonucleotides with EcoRI and HindIII and filling in 5' overhangs with $^{32}$P-dNTPs and Klenow. The oligonucleotides either share several base pairs of homology (oligo 1) or no homology (oligo 2) on each side of the putative cleavage sequence, CAATTG (boxed). The synthetic oligonucleotides (exclusive of the pUC13 polylinker sequences) are underlined. These oligos were incubated with nuclear extracts from Jurkat T cells. Because each 3' end of the double stranded fragments was labeled, when cleavage occurred, two radiolabeled bands were detected on the gel. Both of the oligonucleotides depicted in FIG. 2A were digested (FIG. 2B), suggesting that the six base palindrome CAATTG was sufficient for both recognition and cleavage.

Figure 2C:
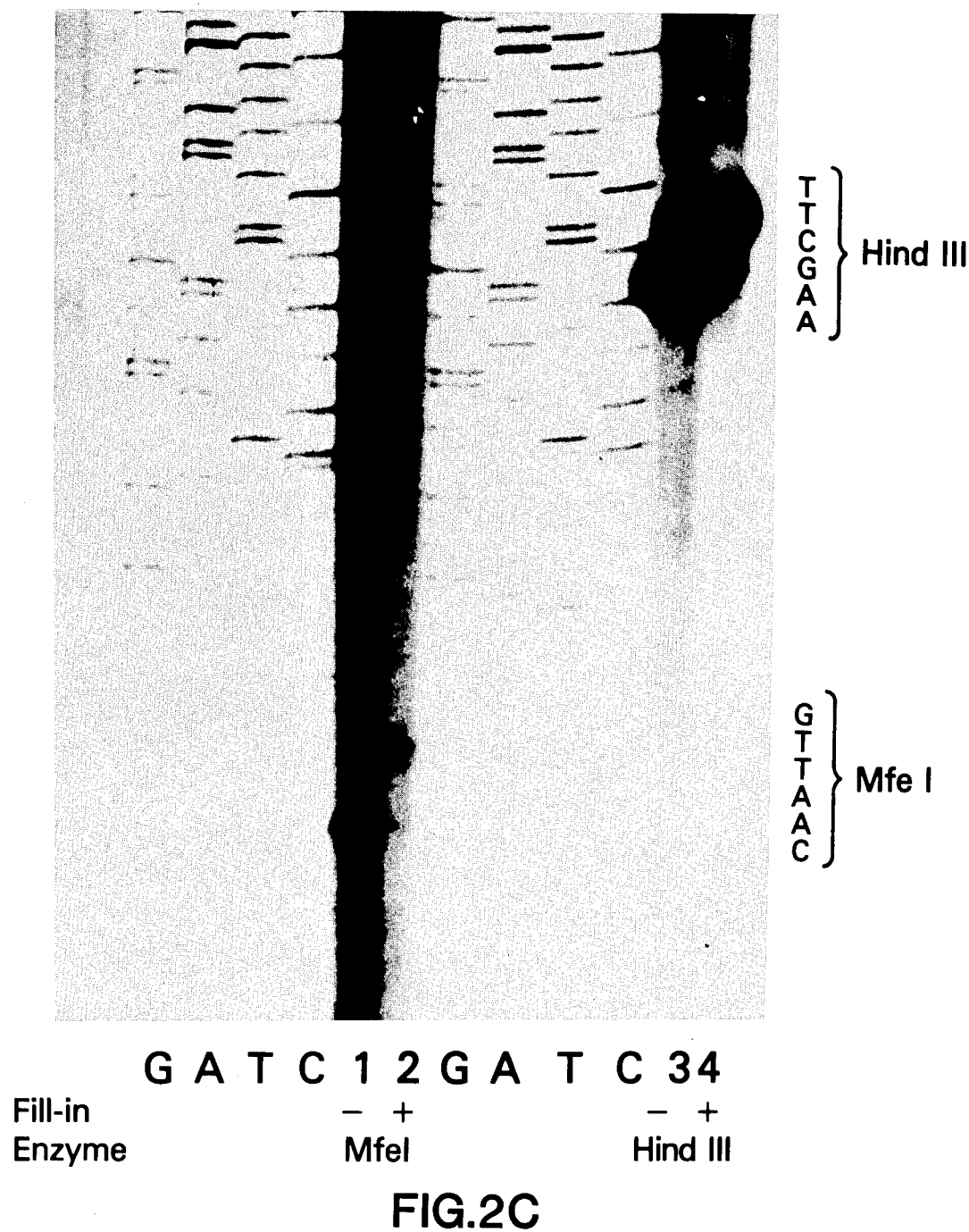
FIG. 2C: Oligo 1 cloned into M13mp19 was annealed to a 17 base pair universal primer and extended through the recognition sequence (CAATTG) with $^{32}$p-deoxynucleotide triphosphates(dNTPs). Jurkat extracts were then added. Half of the resulting reaction was run on a gel (lane 1) and half was treated with a second extension reaction (lane 2). Sequencing reactions of the parent constructs (lanes G, A, T, C) as well as cleavage reactions of a known restriction enzyme, Hind III (lane 3 and 4), were run as controls. Lanes 1 and 2 demonstrate specific cleavage at C'AATTG on both strands.

In FIG. 2C, oligo 1 cloned into M13mp19 was annealed to a primer and double stranded DNA was synthesized using $^{32}$P-dNTPs and Klenow. This DNA was then incubated with nuclear extracts from Jurkat T cells. This resulted in cleavage between the C and the first A in the sequence CAATTG. On the gel the band identified in lane 1 represents a fragment extending from the end of the primer to this cleavage site. Filling in of the cleaved product (lane 2) demonstrated that the enzyme cleaves with a four base 5' overhang. Thus, it is clear that the cleavage site for Mfe I lies between the C and the first A in the palindrome.

In order to exclude the possibility that four or five bases rather than six were sufficient, it was determined that such possibilities as CAAT, AATT, ATTG, CAATT, AATTG were contained multiple times within the sequences of the IL2Rα promoter fragments but the cleavage occurred only once at CAATTG, as shown in FIG. 1. In addition, the possibility of cleavage at sites with purine/pyrimidine substitutions were evaluated by detecting no digestion of pBR322 at its sites corresponding to PyAATTPu (TAATTG), CPuAT-PyG (CGATCG), and CAPuPyTG (CAACTG, CAGCTG, and CAGTTG). Thus, the sequence CAATTG was confirmed to be specifically cleaved by the enzyme. No enzyme with this recognition sequence previously has been reported (Roberts, Nucl. Acid Res. 16:r271-r313, 1988).

Thus, from the Jurkat and MT-2 extracts clear evidence was obtained for a new type II restriction enzyme that digests at a unique recognition site.

Figure 3:
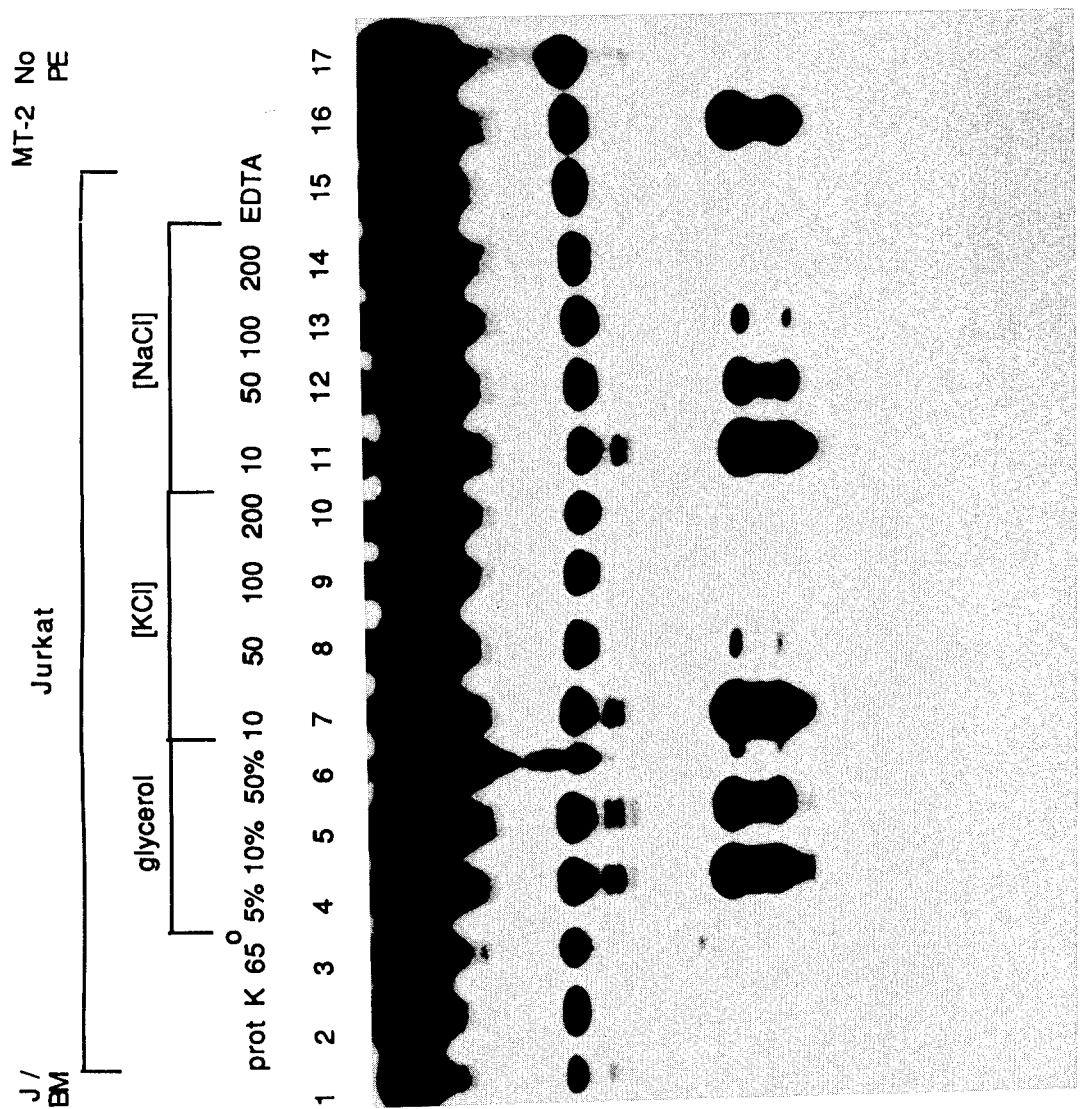
FIG. 3 demonstrates the effect of various conditions on cleavage. Oligo 1 was used as described in FIG. 2. Lane 1, extracts from Jurkat treated with BM cycline; lanes 2 through 15, extracts from Jurkat, not treated with BM cycline; lane 16, extracts from MT-2 cells; lane 17, no protein extracts. Extracts were treated as follows: Lane 2, proteinase K, 670 μg/ml; lane 3, 65° C. for 15 minutes; lane 4, 5% glycerol; lane 5, 10% glycerol; lane 6, 50% glycerol; lane 7, 10 mM KCl; lane 8, 50 mM KCl; lane 9, 100 mM KCl; lane 10, 200 mM KCl; lane 11, 10 mM NaCl; lane 12, 50 mM NaCl; lane 13, 100 mM NaCl; lane 14, 200 mM NaCl; lane 15, 20 mM EDTA.

To further determine whether the mycoplasma was the source of the nuclease, the Jurkat cell line of mycoplasma was cured by BM-cycline (Boehringer Mannheim), according to the manufacturer's directions. Evaluation of nuclear extracts from the cured cell line indicated that the nuclease activity was no longer present (FIG. 3, lane 1 vs. lane 4). In addition, the activity was destroyed by proteinase K (lane 2), and by heating to 65° C. for 15 minutes (lane 3). More complete digestion was obtained at 10 mM NaCl or KCl than at higher salt concentrations (lanes 7-14), and the enzymes could be inactivated by 10 mM EDTA, demonstrating a need for $Mg^{2+}$ or other bivalent cations.

The enzyme which has been designated herein as Mfe I in keeping with traditional nomenclature, is a typical type II enzyme in that it recognizes a short palindromic sequence and cleaves at a site within the recognition site.

Mfe I is extremely valuable for genetic engineering since it cuts at a unique six base pair recognition site and generates cohesive ends which are compatible with EcoRI generated ends. It is also useful for detecting any source which produces Mfe I. A detection assay using *M. fermentans* as an example is now illustrated. Clearly, an analogous assay can be easily developed to identify any source suspected of producing Mfe I.

A diagnostic kit for detecting the presence of a source of Mfe I or Mycoplasma comprises a container containing at least CAATTG as a sequence. Of course, a positive control is routinely used in standard assays.

Illustrative Assay Employing *M. fermentans* As An Example

To assay for the presence of mycoplasma, nuclear extracts of contaminated or putatively contaminated cells are prepared as described herein supra. Synthetic oligo 2 (FIG. 2A) is labeled appropriately, incubated with the extracts, followed by extraction with phenol/chloroform, ethanol precipitation and analysis or 8M urea, 6% polyacrylamide gels. The gel is autoradiographed and then the presence of specific nuclease activity is determined as described herein supra.

It is undertood that the examples and embodiments described herein are for illustrative purposes only and that various modifications or changes in light thereof will be suggested to persons skilled in the art and are to be included within the spirit and purview of this application and scope of the appended claims.

What is claimed is:

1. An isolated, biologically pure endonuclease which specifically recognizes the nucleotide sequence CAATTG and cleaves between nucleotides CA of said sequence.

2. The endonuclease of claim 1 produced by growing *Mycoplasma fermentans* in a cell culture and recovering from extracts thereof said endonuclease by conventional purification techniques.

* * * * *